United States Patent
Wu

(10) Patent No.: US 9,851,261 B2
(45) Date of Patent: Dec. 26, 2017

(54) SYSTEM AND APPARATUS FOR DETERMINING AMBIENT TEMPERATURES FOR A FLUID ANALYTE SYSTEM

(71) Applicant: Bayer HealthCare LLC, Whippany, NJ (US)

(72) Inventor: Mu Wu, Hopewell Junction, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 719 days.

(21) Appl. No.: 14/323,274

(22) Filed: Jul. 3, 2014

(65) Prior Publication Data

US 2014/0314119 A1  Oct. 23, 2014

Related U.S. Application Data

(62) Division of application No. 13/234,268, filed on Sep. 16, 2011, now Pat. No. 8,801,275.

(Continued)

(51) Int. Cl.
*G01K 1/20* (2006.01)
*G01K 1/08* (2006.01)
(Continued)

(52) U.S. Cl.
CPC ............ *G01K 1/20* (2013.01); *A61B 5/14532* (2013.01); *G01K 7/42* (2013.01); *G01N 33/48785* (2013.01)

(58) Field of Classification Search
CPC .. G01K 1/20; G01K 3/04; G01K 3/06; G01K 3/08; G01K 3/10; G01K 3/14; G01K 1/08; G01K 7/16; G01K 11/00; G01K 13/12

(Continued)

(56) References Cited

U.S. PATENT DOCUMENTS 3,967,188 A * 6/1976 Spencer ................. G01D 3/036
 323/367
4,407,141 A * 10/1983 Paddock ................. F25D 29/00
 236/94

(Continued)

FOREIGN PATENT DOCUMENTS

GB 2 091 882 A 8/1982
WO WO 2010/048294 4/2010

OTHER PUBLICATIONS

International Search Report dated Dec. 22, 2011 for International Application No. PCT/US2011/051933, 3 pages.

(Continued)

*Primary Examiner* — Gail Kaplan Verbitsky
(74) *Attorney, Agent, or Firm* — Nixon Peabody LLP

(57) ABSTRACT

A system and method for rapidly determining ambient temperature in a fluid-analyte meter. The meter includes a housing defining an interior space and an area for receiving a fluid sample. A processor and a first temperature sensor are disposed within the interior space of said the housing. A second temperature sensor is disposed on the housing. One or more processors are configured to determine a first temperature value from temperature data received from the first temperature sensor. The processor(s) are also configured to apply a variable current to a temperature-adjustment source such that the second temperature sensor is adjusted to a predetermined steady-state temperature value different from the first temperature value. The processor(s) are further configured to determine an ambient temperature of an exterior space of the housing based on the applied variable current, pre-determined steady-state temperature, and received first temperature values.

20 Claims, 3 Drawing Sheets

Related U.S. Application Data

(60) Provisional application No. 61/385,749, filed on Sep. 23, 2010.

(51) Int. Cl.
  *G01K 7/16* (2006.01)
  *G01K 11/00* (2006.01)
  *G01K 13/12* (2006.01)
  *G01K 7/42* (2006.01)
  *G01N 33/487* (2006.01)
  *A61B 5/145* (2006.01)

(58) Field of Classification Search
  USPC ... 374/109, 102, 100, 1, 183, 185, 208, 163, 374/31–39
  See application file for complete search history.

(56) References Cited

U.S. PATENT DOCUMENTS

| | | | | |
|---|---|---|---|---|
| 4,501,952 A * | 2/1985 | Lehrke | ............... | B05B 7/22 165/156 |
| 4,566,342 A * | 1/1986 | Kurz | ............... | G01N 1/2035 73/863.03 |
| 4,859,834 A * | 8/1989 | Hausler | ............... | G05D 23/24 219/494 |
| 5,031,126 A * | 7/1991 | McCulloch | ............... | G01F 1/698 340/622 |
| 5,356,217 A | 10/1994 | Sheffield | ............... | 374/45 |
| 5,587,926 A * | 12/1996 | Chiu | ............... | E03F 7/00 702/179 |
| 5,772,321 A | 6/1998 | Rhodes | ............... | 374/44 |
| 5,876,120 A * | 3/1999 | Lee | ............... | G01J 5/14 374/133 |
| 6,635,167 B1 | 10/2003 | Batman et al. | | |
| 6,753,187 B2 | 6/2004 | Cizdziel et al. | ............... | 436/169 |
| 6,905,242 B2 | 6/2005 | Heuer et al. | ............... | 374/142 |
| 7,027,834 B2 | 4/2006 | Soini et al. | ............... | 455/556.1 |
| 7,140,263 B2 | 11/2006 | Beversdorf | ............... | 73/861 |
| 7,785,001 B2 | 8/2010 | Tao et al. | ............... | 374/117 |
| 8,182,143 B2 * | 5/2012 | Fleming | ............... | G01K 13/02 374/138 |
| 8,201,992 B2 | 6/2012 | Horovitz et al. | ............... | 374/29 |
| 8,313,237 B2 * | 11/2012 | Jetter | ............... | A61B 5/14532 374/110 |
| 8,617,381 B2 | 12/2013 | Sun et al. | ............... | 205/775 |
| 8,649,997 B2 | 2/2014 | Farrell et al. | ............... | 702/130 |
| 9,097,650 B2 * | 8/2015 | Sun | ............... | A61B 5/01 |
| 2002/0037238 A1 | 3/2002 | Haar et al. | | |
| 2008/0173552 A1 | 7/2008 | Wu et al. | ............... | 205/775 |
| 2009/0028208 A1 | 1/2009 | Martin | ............... | 374/1 |
| 2009/0100906 A1 | 4/2009 | Bonne | ............... | 73/25.03 |
| 2010/0283488 A1 | 11/2010 | Nakamura et al. | ............... | 324/692 |
| 2010/0307916 A1 | 12/2010 | Ramey et al. | ............... | 204/402 |
| 2010/0319436 A1 | 12/2010 | Sun et al. | ............... | 73/61.46 |
| 2010/0324398 A1 | 12/2010 | Tzyy-Ping | ............... | 600/365 |
| 2011/0191059 A1 | 8/2011 | Farrell et al. | ............... | 702/130 |
| 2012/0177082 A1 | 7/2012 | Kim | ............... | 374/45 |
| 2013/0158376 A1 | 6/2013 | Hayter et al. | ............... | 600/347 |
| 2014/0066726 A1 | 3/2014 | Costello | ............... | 600/302 |
| 2014/0203184 A1 * | 7/2014 | Purdy | ............... | G01N 33/18 250/393 |
| 2015/0003491 A1 * | 1/2015 | Matsumoto | ............... | G01K 1/20 374/1 |
| 2015/0293055 A1 * | 10/2015 | Sun | ............... | A61B 5/01 204/408 |

OTHER PUBLICATIONS

Written Opinion of the International Searching Authority dated Dec. 22, 2011 for International Application No. PCT/US2011/051933, 8 pages.

\* cited by examiner

Fig. 5A
Fig. 5B
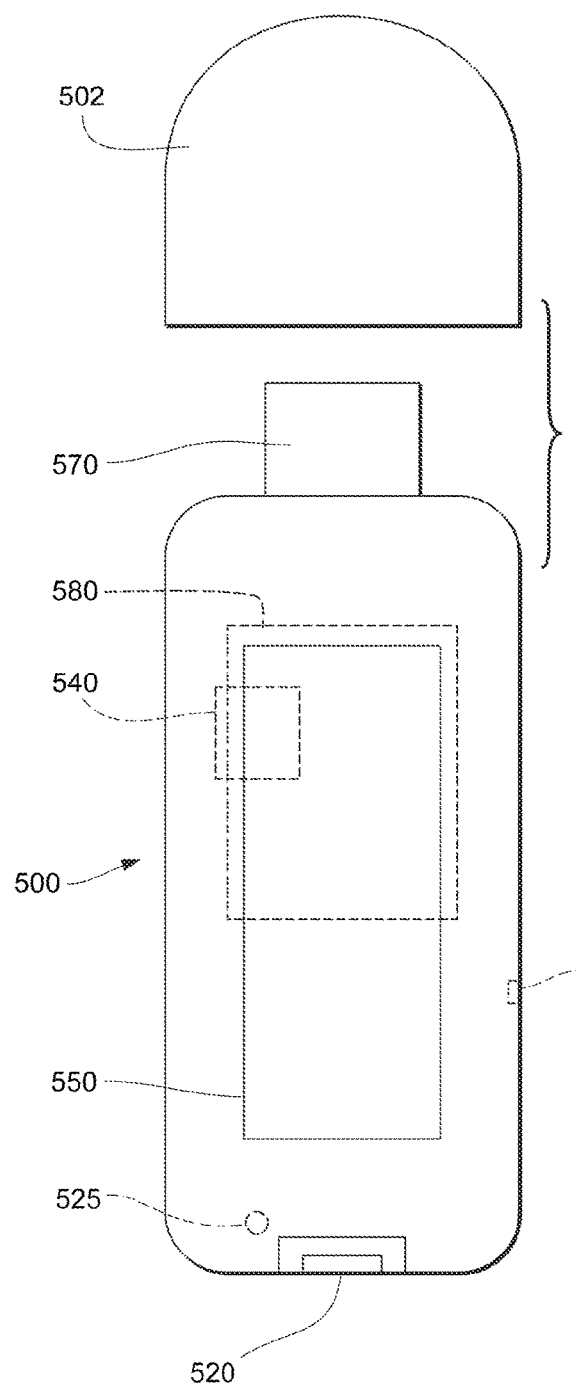
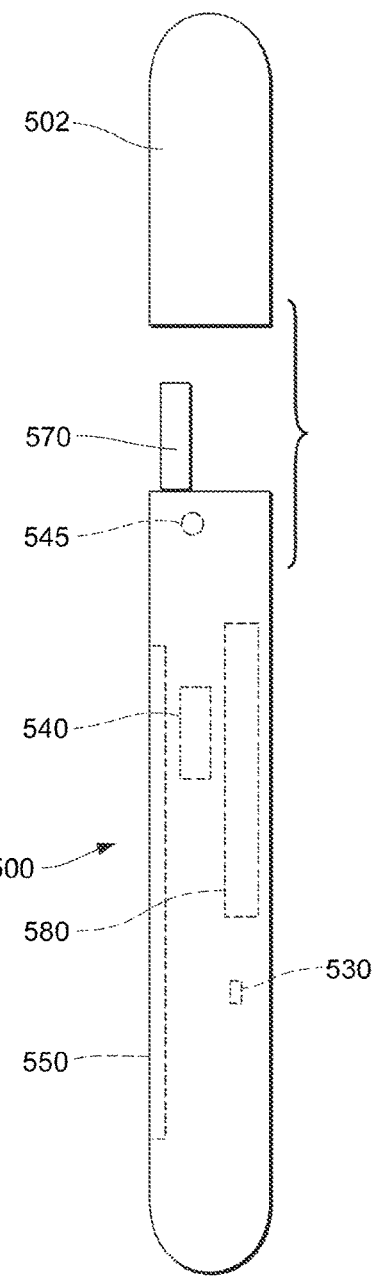

SYSTEM AND APPARATUS FOR DETERMINING AMBIENT TEMPERATURES FOR A FLUID ANALYTE SYSTEM

CROSS REFERENCE TO RELATED APPLICATIONS

This application is a divisional of U.S. patent application Ser. No. 13/234,268, filed Sep. 16, 2011, now allowed, which claims the benefit of and priority to U.S. Provisional Patent Application No. 61/385,749, filed Sep. 23, 2010, each of which are hereby incorporated by reference herein in their entireties.

FIELD OF THE INVENTION

The present invention generally relates to systems for determining ambient temperature, and more particularly, to the determination of ambient temperature for a device in which the temperature inside the device is different from the ambient temperature.

BACKGROUND

The quantitative determination of analytes in body fluids is of great importance in the diagnoses and maintenance of certain physiological conditions. For example, lactate, cholesterol, and bilirubin should be monitored in certain individuals. In particular, determining glucose in body fluids is important to individuals with diabetes who must frequently check the glucose level in their blood to regulate the carbohydrate intake in their diets. The results of such tests can be used to determine what, if any, insulin or other medication needs to be administered. In one type of testing system, test sensors are used to test a fluid such as a sample of blood.

Measurement of blood glucose concentration is typically based on a chemical reaction between blood glucose and a reagent. The chemical reaction and the resulting blood glucose reading as determined by a blood glucose meter is temperature sensitive. Therefore, a temperature sensor is typically placed inside the blood glucose meter. The ambient temperature and reagent temperature are then extracted using the temperature sensor readings. The calculation for blood glucose concentration in such meters typically assumes that the temperature of the reagent is the same as the temperature reading from the test sensor placed inside the meter. However, if the actual temperature of the reagent and the test sensor are different, the calculated blood glucose concentration will not be as accurate. An increase in temperature or the presence of a heat source within a blood glucose meter will generally result in erroneous blood glucose measurements. Furthermore, the thermal properties of a blood glucose meter often render the system slow to respond to environmental changes such as a change in temperature.

SUMMARY

According to one embodiment, a fluid-analyte meter is configured to rapidly determine ambient temperature. The meter includes a housing defining an interior space and an exterior ambient space. A processor is disposed within the housing. A controller is disposed within the housing. The controller is communicatively connected to the processor. A first temperature sensor is disposed within the interior space of the housing. The second temperature sensor is disposed on the housing. The second temperature sensor is communicatively connected to the controller. A temperature-adjustment source is disposed on the housing. The temperature-adjustment source is configured to create a convective zone about the second temperature sensor. The controller is configured to transmit instructions for supplying a variable current to the temperature-adjustment source such that the temperature-adjustment source adjusts the second temperature sensor to a predetermined steady-state temperature value different from a first temperature value. The first temperature value is based on first temperature data received via the controller from the first temperature sensor. The controller is further configured to receive second temperature data from the second temperature sensor. The controller or the processor are configured to determine an ambient temperature of the exterior ambient space based on the supplied variable current, predetermined steady-state temperature, and first temperature values.

According to another embodiment, a method for rapidly determining ambient temperature in a fluid-analyte meter includes providing a meter including a housing. A first temperature sensor is disposed within an interior space of the housing. A second temperature sensor is disposed on the housing. A temperature-adjustment source is disposed near the second temperature sensor. A first temperature value is determined from first temperature data received via the first temperature sensor. A variable current is applied to the temperature-adjustment source such that the second temperature sensor is adjusted to a predetermined equilibrium temperature value different from the first temperature value. A second temperature value is determined from second temperature data received from the second temperature sensor. An ambient temperature of an exterior space of said fluid-analyte meter is determined, via one or more processors, based on the variable current and the determined first and second temperature values.

According to another embodiment, a portable meter configured to rapidly determine ambient temperature includes a housing defining an interior space and an area for receiving a fluid sample. A first processing unit and a first temperature sensor are disposed within the interior space of the housing. A second temperature sensor is disposed on the housing. The first processing unit or another processing unit is configured to determine a first temperature value from temperature data received from the first temperature sensor. A variable current is applied to a temperature-adjustment source such that the second temperature sensor is adjusted to a predetermined steady-state temperature value different from the first temperature value. An ambient temperature of an exterior space of the housing is determined based on the applied variable current, the pre-determined steady-state temperature value, and the received first temperature value. The ambient temperature value is determined in less than about sixty seconds.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 5A illustrates a portable fluid analyte device with a USB interface according to another embodiment.

FIG. 5B illustrates a side view of the portable device of FIG. 5A.

Figure 1:
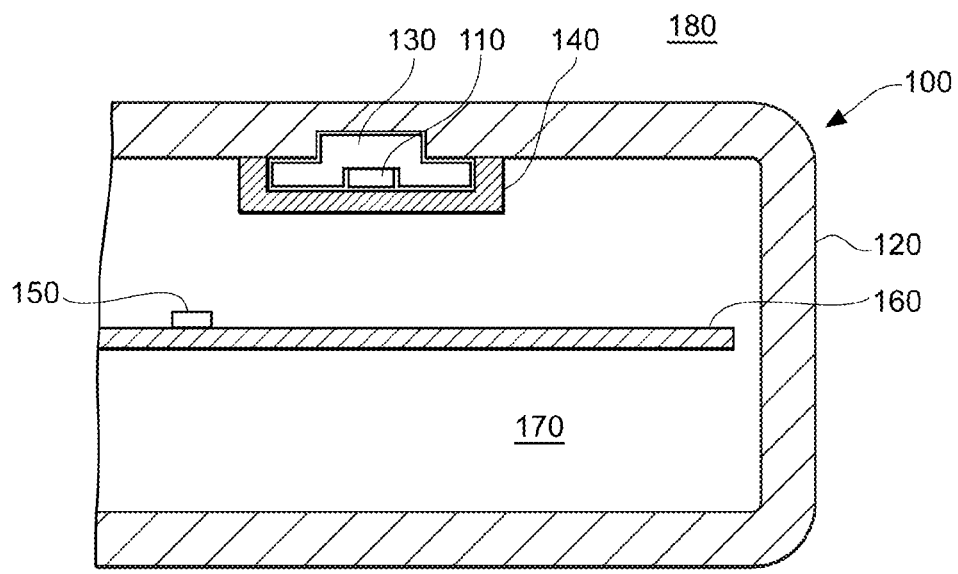
FIG. 1 illustrates a temperature sensor disposed on a casing of a meter according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION

Generally, a test sensor is employed to collect a fluid sample, such as blood, and a blood glucose meter measures a reaction between the glucose in the fluid sample with a reagent on the test sensor to calculate a corresponding blood glucose concentration. The temperature of the reagent affects the reaction between the glucose and the reagent. As such, the temperature of the reagent also affects the blood glucose concentration calculated by the blood glucose meter. For certain embodiments, such as, where the reagent area of the test sensor is located outside the blood glucose meter, the temperature of the reagent can be assumed to be substantially equal to the ambient temperature in or surrounding the meter. Temperature sensing elements in the blood glucose meter can provide an estimate of the ambient temperature, which can then be used in the calculation of the blood glucose concentration. However, the blood glucose meter includes various heat-generating elements, which along with various external heat sources, can cause the temperature measured by the temperature sensing elements in the meter to differ from the ambient temperature. When the temperature measured by the temperature sensing elements does not provide an accurate estimate of the ambient temperature, inaccuracies are introduced into the determination of the blood glucose concentration.

To achieve more accurate determinations of fluid-analyte concentrations (e.g., blood glucose concentration), different temperature sensor configurations can be used to determine ambient temperature for an instrument (e.g., blood glucose meter, other fluid-analyte meter). In one embodiment, a resistance temperature detector (RTD) sensor can be embedded in, or otherwise disposed on the interior or exterior surface of an instrument casing or shell. This can be beneficial for determining ambient temperature by providing temperature-related data, which can then be adjusted to compensate for any of a number of factors, such as reagent errors caused by ambient temperature variations, temperature variations caused by internal heating of the instrument by internal electronic components, or nearby localized heating from external sources.

In certain embodiments, test sensors (e.g., test strips) are used in conjunction with a fluid-analyte meter. In such embodiments, a test strip may include electrical components for interfacing the test strip with a fluid-analyte meter. Test strips tend to quickly equilibrate to the ambient temperature of the testing environment, such as areas within or surrounding a fluid-analyte meter. To accurately determine analyte concentrations for test samples received via a test strip, it is beneficial to correctly estimate the ambient temperature particularly where direct temperature measurement on a test strip is not possible. It is also desirable for the ambient temperature estimate to be made quickly and accurately, particularly for meters exposed to testing environments that change often.

Figure 2:
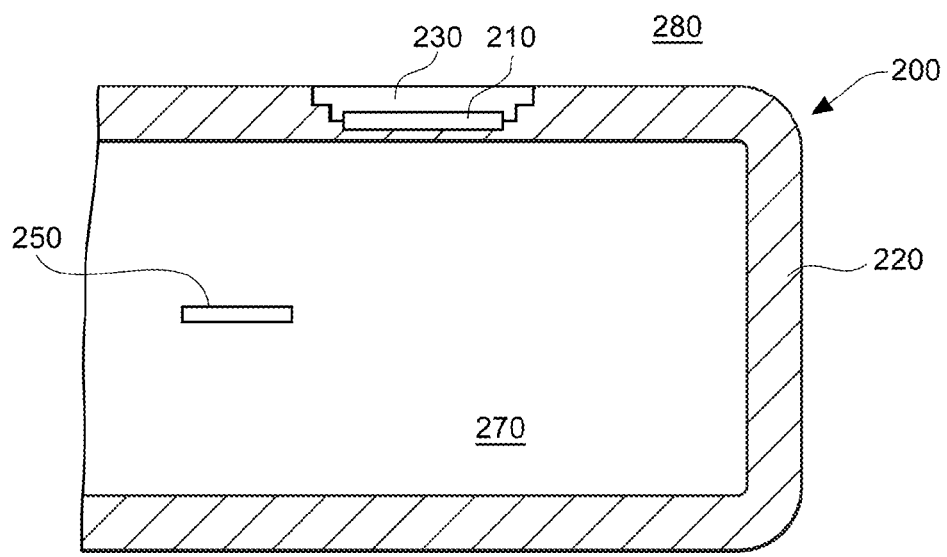
FIG. 2 illustrates a temperature sensor disposed on a casing of a meter according to another embodiment.

Exemplary and non-limiting temperature sensor embodiments for determining the ambient temperature at or surrounding an instrument, such as a fluid analyte meter, are illustrated in FIGS. 1 and 2. Non-limiting systems that may employ these temperature sensor embodiments are described below in connection with FIGS. 3-5.

Referring now to FIGS. 1 and 2, non-limiting and exemplary temperature sensor configurations are illustrated for determining ambient temperature using an RTD sensor embedded in or otherwise disposed on the interior or exterior of a fluid-analyte meter. One or more RTD sensors may be disposed on, or at least partially embedded in, the shell or casing of the fluid analyte meter. The RTD sensor embodiments described herein provide a relatively quick and accurate estimation of ambient temperature, despite, for example, the ambient temperature being unknown. These RTD sensor configurations are at least partially based on convection around the meter due to temperature differences between the meter and its surrounding environment and increasing the temperature of the RTD sensor.

In certain embodiments, either the RTD sensor, or a separate heat source disposed near or adjacent to the RTD sensor, can be configured to generate heat flow into (e.g., from the ambient environment to the inside the meter) and out of the meter (e.g., from inside the meter to the ambient environment). For example, a current may be applied to the RTD sensor or the heat source to heat the RTD sensor to a temperature that is higher than the internal temperature of the meter. The benefit of heating the RTD sensor to a temperature above the internal temperature of the meter is to create air flow about the meter, rather than the RTD sensor measuring a surface temperature based on stagnant air immediately adjacent the meter casing. Through localized heating of the RTD sensor, localized convection is promoted around the meter such that the heat flow or heat loss from the RTD sensor allows an accurate determination of ambient temperature for use in any subsequent determinations of fluid-analyte concentration based on the determined ambient temperature.

The internal temperature of a meter may be determined by the RTD sensor itself, or desirably by a separate temperature sensor (e.g., another RTD, a thermistor, a thermocouple, semiconductor diodes) located internal to or within the meter. In certain embodiments, a very low current may be supplied to a separate temperature sensor that is used to determine the internal temperature of a meter such that the separate temperature sensor does not raise the temperature of the meter. When the RTD sensor is used to determine the internal temperature of the meter, a similar procedure is used where a very low current is applied to the RTD sensor before a higher current is applied for heating purposes. Also, similarly, the very low current that is applied is such that the RTD sensor during the temperature determination stage contributes a negligible temperature rise to the meter. As discussed previously, the internal temperature of a meter can increase due to external factors along with heat generated by certain electronic components of the meter, such as a display, a microprocessor, or other electronic components.

The thermal mass of a meter (see, e.g., meters 100, 200, 300), such as, for example, a fluid-analyte meter, is typically much larger than the thermal mass of an RTD sensor that is used to determine ambient temperature. The RTD sensor or heat source will therefore generally provide localized heating in a small region of the meter in the vicinity of the heat source. Thus, the localized heating is not expected to significantly affect the internal temperature of the meter. However, it can be desirable to locate the RTD sensor or similar heat sources away from elements on the meter that are heat-sensitive.

In certain embodiments, an RTD sensor is desirably heated so that the RTD sensor maintains a constant or almost constant temperature above the internal temperature of the meter. Heating of the RTD sensor occurs by applying a large current (e.g., about 1 mA to about 200 mA) to the sensor. The value of the applied current depends on the temperature desired for the RTD sensor. Generally, an RTD sensor that is used to measure temperature only is powered by low currents (e.g., less than about 0.1 mA) sufficient to obtain a value that correlates with a temperature.

Due to the relatively high current that may be used to heat an RTD sensor operating in a dual role as a temperature sensor and a heat source, the RTD sensor may be configured in a standard four-wire mode, with four wires connected to a single, two-terminal device such that two wires are attached to each end or terminal of the RTD sensor. Two of the four wires are then configured in a loop or circuit that applies the high current to the RTD sensor, via, for example, a programmable current source. The other two wires can be configured in a loop or circuit that measures the voltage across the RTD sensor. One of the benefits of a four-wire configuration for measuring voltage across an RTD sensor is that it minimizes errors that can be caused by lead wires to the RTD sensor.

A closed-loop controller, such as a proportional-integral-derivative controller (PID controller), can be desirable for controlling the RTD sensor because the device includes feedback mechanisms useful for maintaining the temperature of the RTD sensor at a constant value above the internal temperature of the meter. For example, a PID controller may be used to apply a variable current to an RTD sensor that ranges anywhere from about 1 mA to about 200 mA. Furthermore, depending on the desired temperature increase above the internal meter temperature, it can take a period of time for a heat flux from the RTD sensor to the inside of the meter, $\Phi_{INSIDE}$, to reach a steady state, or equilibrium, and for the temperature difference between the RTD sensor and the internal meter temperature to be maintained, based on the relationship of $T_{RTD}-T_{AMBIENT}$ being equal to an approximately constant value. In one embodiment, a temperature increase in the RTD sensor of approximately 5 degrees Celsius over the internal meter temperature is attained in less than about one minute, with the ambient temperature being accurately determining within about ±0.5 degrees Celsius. In another non-limiting and exemplary embodiment, a temperature increase in the RTD sensor of approximately 2.5 degrees Celsius over the internal meter temperature is attained in less than about 30 seconds, with the ambient temperature being accurately determining within about ±1 degree Celsius.

The heat flux between the inside of the meter and the exterior ambient environment is in a dynamic state until the desired constant temperature difference is reached, at which point the heat flux is desirably maintained in a steady state condition. The time to reach the steady state condition can be affected by a number of factors associated with the physical design of the fluid-analyte meter including meter casing material properties (e.g., thermal conductivity) and/or structural aspects of the meter (e.g., meter casing thickness). It is contemplated that it may be desirable for an instrument, such as a fluid-analyte meter, to be constructed such that the time needed for the RTD to reach steady state, or thermal equilibrium, is minimized. For example, the meter casing or shell can be designed to reduce the thermal mass around the RTD. Furthermore, the location of the RTD on or within the meter casing can be chosen to minimize the chance that the user of the meter touches or is near the RTD during meter operation.

By maintaining the temperature of an RTD sensor at an approximately constant value above the internal temperature of the meter, a heat flux from the RTD sensor to the inside of the meter, $\phi_{INSIDE}$, is expected to remain approximately the same. Meanwhile, a heat flux going from the RTD sensor to the ambient environment, $\phi_{AMBIENT}$, is expected to be higher. If the total amount of heat, $\phi_{TOTAL}$, is known and with $\phi_{INSIDE}$ staying constant, then the value for $\phi_{AMBIENT}$ can be determined using the relationships described in Equations 1 and 2:

$$\phi_{TOTAL}=\phi_{INSIDE}+\phi_{AMBIENT} \quad \text{(Equation 1)}$$

$$\phi_{AMBIENT}=\phi_{TOTAL}-\phi_{INSIDE} \quad \text{(Equation 2)}$$

The value of $\phi_{TOTAL}$ can be determined or approximated based on the input energy to the RTD sensor and can be expressed by the product of the input voltage and current applied to the RTD sensor for bringing the RTD sensor to a steady state temperature value above the internal meter temperature. Using Equation 2, $\phi_{AMBIENT}$ can be determined from the known information about $\phi_{TOTAL}$ and $\phi_{INSIDE}$ at the steady state temperature for the RTD sensor. Equations 3 and 4 can then be applied to determine the ambient temperature, $T_{AMBIENT}$:

$$\phi_{AMBIENT}=K_{AMBIENT}(T_{RTD}-T_{AMBIENT}) \quad \text{(Equation 3)}$$

$$T_{AMBIENT}=T_{RTD}-(\phi_{AMBIENT}/K_{AMBIENT}) \quad \text{(Equation 4)}$$

$K_{AMBIENT}$ is a fixed coefficient related to the surface area affected by the heat flow. The coefficient is derived by placing an instrument containing the RTD sensor (e.g., a fluid-analyte meter) into an environment having a known ambient temperature. The instrument is then calibrated to determine $K_{AMBIENT}$ experimentally. The calibration process is useful because the value of $K_{AMBIENT}$ will vary due to mechanical design changes and variations in the assembly of the meter and RTD sensor. These factors make it desirable to apply a calibration process for determining the instrument-specific (e.g., meter-specific) value of $K_{AMBIENT}$.

The embodiments in FIGS. 1 and 2 are illustrated using an RTD sensor, which is a low-resistance temperature measurement device that has desirable applications for precision measurements. As discussed above, an RTD sensor can be heated by applying a current across the RTD sensor, and thus, can also operate as a heat source. In certain embodiments, a controllable heat source separate from, but near or immediately adjacent to a temperature sensor, can be used. Such a configuration allows other types of temperature sensors known in the art to be combined with the heat source so that a constant temperature above the internal temperature of the instrument can be maintained while generating a heat flux across the interior and exterior of the instrument.

Referring now in more detail to FIG. 1, a meter 100 is illustrated having two temperature sensors 110, 150, including one RTD sensor 110 for determining ambient temperature. The meter 100 includes a housing 120 (e.g., protective casing or shell) defining an inside area 170 of the meter 100. The inside area 170 can include a printed circuit board ("PCB") 160 having electronics associated with the meter disposed thereon. Such electronics may include a controller for the meter 100. The PCB 160 can have an internal temperature sensor 150, such as a thermistor or other temperature sensing device, disposed thereon or disposed within the electronics on the PCB 160. The PCB 160 can be conductively and/or communicatively connected to one or both of sensors 110, 150. The housing 120 may be constructed of a polymer material or other suitable materials for an electronic fluid-analyte measuring instrument (e.g., a blood glucose meter).

The housing 120 can include an interior surface exposed to the inside area 170 and an exterior surface exposed to an ambient environment 180. The interior surface of the housing 120 can include an RTD sensor 110 disposed between the housing 120 and an insulating cover 140 (e.g., a cover layer) that isolates the RTD sensor 110 from the inside area 170. In certain embodiments, the RTD sensor can have the dual tasks of operating as a temperature sensor and as a heat source when high currents are applied to the sensor. The isolation of the RTD sensor 110 is directed to shielding the RTD sensor 110 from temperature fluctuations in the inside area 170 and to shield the inside area 170 from temperature increases when the RTD sensor 110 operates as a heat source. The RTD sensor 110 can also be at least partially encased or cradled within a metal layer 130 (e.g., grommet-like device) configured to surround the RTD sensor 110 on multiple sides and further configured in certain embodiments to be embedded with the casing. In certain embodiments, the insulating cover 140 isolates both the RTD sensor 110 and the metal layer 130. As the metal layer 130 is a conductive layer, it can establish the heat flux from the RTD sensor 110, through the housing 120, and to the ambient environment 180. The metal layer 130 can also establish a heat flux from the ambient environment 180, through the RTD sensor 110, and into the inside area 170.

It is contemplated that in certain situations, the internal temperature sensor 150 can provide an accurate assessment of ambient temperature. For example, after the meter has been turned on following a significant period of little energy consumption by the meter electronics, negligible internal heating of the meter 100 would be expected, and sensor 150 can be expected to be at or near an ambient temperature. However, after certain heat-generating operations, the internal temperature sensor 150 alone may not be able to provide an accurate estimation of ambient temperature. As described above, the configuration described for RTD sensor 110 can be desirable because it allows for an indirect determination of the ambient temperature in ambient environment 180. Furthermore, it allows localized heating of the housing 120, which further encourages air flow or circulation of air along the exterior of the housing 120, or a more accurate exposure to the ambient environment 180.

An RTD sensor normally exhibits low resistance characteristics. However, when current is applied to the RTD sensor 110 in FIG. 1, the RTD sensor 110 generates heat and the temperature of the RTD sensor 110 increases, particularly as the period of time of current application increases. Furthermore, as the temperature of the RTD sensor 110 rises, so does the resistance, which can lead to greater temperature increases. For example, in certain embodiments, an RTD sensor, such as a 100 ohm platinum RTD sensor, may be calibrated to exhibit approximately 100 ohms of resistance at zero degrees Celsius. The same RTD sensor may also exhibit approximately 120 ohms of resistance when the temperature increases to approximately 50 degrees Celsius. It is contemplated that different RTD sensors may be used in the embodiments described herein. For example, in one non-limiting embodiment it may be desirable to use a commercially-available Pt-385 RTD sensor. Another non-limiting example of an RTD sensor is the OMEGAFILM® flat profile thin film platinum sensor with ceramic base and glass coating, Model No. F2020-100-B-100, as manufacturer by Omega Engineering, Inc. of Stamford, Conn., USA. Again, different RTD sensors can be used, or different types of temperature sensors in combination with a nearby heat source.

Referring now to FIG. 2, another embodiment is illustrated of a meter 200 having two temperature sensors 210, 250, including an RTD sensor 210 for determining ambient temperature. The meter 200 includes a housing 220 (e.g., protective casing or shell) defining an inside area 270 of the meter 200. The inside area 270 can include an internal temperature sensor 250, such as a thermistor or other temperature sensing device, disposed within the inside area 270. The housing 220 can be constructed of a polymer material or other suitable materials for an electronic fluid-analyte measuring device. The housing 220 can include an interior surface exposed to the inside area 270 and an exterior surface exposed to an ambient environment 280. The housing 220 can include an RTD sensor 210 embedded between the interior and exterior surface of the housing 220. The housing material may have insulative properties that isolate the RTD sensor 210 from the inside area 270. In certain embodiments, the RTD sensor 210 can have the dual tasks of operating as a temperature sensor with the application of low, constant currents and as a heat source with the application of high variable currents for maintaining a constant temperature above the internal meter temperature. The RTD sensor 210 can be at least partially encased or covered by a metal layer 230 (e.g., metal cover) configured to surround the upper surfaces of RTD sensor 210 and further configured for certain embodiments to be exposed to the ambient environment 280. The metal layer 230 may be flush or recessed below the exterior surface of the housing 220. It is also contemplated that the metal layer 230 may extend out from the exterior surface of the housing 220. As the metal layer 230 is a conductive layer, it can be used to establish the heat flux from the RTD sensor 210 to the ambient environment 280. The metal layer 230 can also establish a heat flux from the ambient environment 280, through the RTD sensor 220, and into the inside area 270.

In the embodiments discussed above in FIGS. 1 and 2, values obtained from certain features of meters 100, 200 can be used in Equations 1 through 4 to calculate the temperature of ambient environments 180, 280. For example, $T_{RTD}$ represents the ambient temperature determined using the temperature information obtained from RTD sensor 110 or RTD sensor 210. $T_{INSIDE}$ represents the internal or inside temperature of the meters 100, 200 determined using the temperature information obtained from the internal temperature sensor 150 or the internal temperature sensor 250. The temperature, $T_{RTD}$, of the RTD sensors 110, 210 is controlled by applying a variable current to the sensor via a controller or otherwise so that the sensor reaches and maintains a steady-state temperature value of $T_{INSIDE}$ plus a fixed constant value. The fixed constant may vary depending on the application. In certain embodiments, the fixed constant value may range from 1 to 10 degrees Celsius. That is, the temperature of the RTD sensor 110, 210, or $T_{RTD}$, is increased or heated by a fixed amount that can range from approximately 1 to 10 degrees Celsius above the temperature, $T_{INSIDE}$, determined by the internal temperature sensors 150, 250. In certain embodiments, the fixed constant may be greater than or less than the 1 to 10 degree Celsius range. In certain embodiments, the fixed constant of $T_{RTD}$ at its steady state value minus $T_{INSIDE}$ is equal or slightly greater than the maximum internal temperature rise of the meter 100, 200. It is also contemplated that in certain embodiments, the temperature of RTD sensors 110, 210 may be maintained at a temperature that is lower than the internal temperature of the meter by using thermoelectric cooling, such as, through the Peltier effect. By applying thermoelectric cooling, the temperature of the RTD sensor may be decreased by up to several degrees and maintained a constant temperature that is lower than the internal meter temperature. As discussed herein, the internal temperature of the meter may be affected by many elements, including internal electronic components in the meter or nearby heat sources that cause heat to flow through the meter housing and into the inside areas of the meter.

As discussed above in Equations 1 and 2, total heat flux is equal to the sum of $\phi_{INSIDE}$ (i.e., the heat flow from the RTD sensor to the inside area of the meter) and $\phi_{AMBIENT}$ (i.e., the heat flow from the RTD sensor to the ambient environment). The heat flux from the RTD sensor to the inside area of the meter and the heat flux from the RTD sensor to the ambient environment can be represented by the relationships described in Equations 5 and 6:

$$\phi_{INSIDE} = k_{INSIDE} A_{INSIDE} (T_{RTD} - T_{INSIDE}) \quad \text{(Equation 5)}$$

$$\phi_{AMBIENT} = k_{AMBIENT} A_{AMBIENT} (T_{RTD} - T_{AMBIENT}) \quad \text{(Equation 6)}$$

where $A_{INSIDE}$ is the internal surface area over which the heat flows, $A_{AMBIENT}$ is the external surface area over which the heat flows, and $k_{INSIDE}$ and $k_{AMBIENT}$ are fixed coefficients. The internal surface area, $A_{INSIDE}$, in the FIG. 1 and FIG. 2 embodiments can be estimated to be the surface area of metal layer 130, 230 facing the respective inside areas 170, 270 of the meter 100, 200. The external surface area, $A_{AMBIENT}$, can be estimated to be the surface area of metal layer 130, 230 facing the respective ambient environments 180, 280 of the meter 100, 200.

In one non-limiting embodiment of a temperature sensor configuration for a fluid-analyte meter, a 2×2×0.8 mm thin-film RTD sensor (e.g., Omega Model No. F2020-100-B-100) is embedded into the outer shell or casing of the meter and has a resistance of 100 ohms at zero degrees Celsius. A metal layer or heat radiator (e.g., 130, 230) is fabricated from a heat-conducting material, such as copper, and is fitted into the exterior shell over the RTD sensor such that part of the metal layer is along the exterior surface of the shell for the meter. An internal temperature sensor (e.g., 150, 250) such as a chip thermistor is located within the inside area of the meter and has a value of 50 kOhm at 25 degrees Celsius. The chip thermistor can be mounted, for example, to a PCB within the meter. The outer casing or shell of the meter may be fabricated of a plastic material, and one non-limiting embodiment has dimensions of approximately 110×60×20 mm. The internal temperature of the meter may rise due to various heat sources associated with the meter, including various electrical components prone to heat rise. The typical heat generated within a meter or other type of handheld electronic instrument can come from various sources and can be approximated by the application of 100 mW to 5 W of total power to various resistive components within the handheld device during its operation. This heat can raise the internal temperature of the exemplary meter by approximately 5 to 30 degrees Celsius above the ambient temperature. Furthermore, the internal temperature may be fluctuating as the operations of the meter change. As described earlier, a PID controller may be used to supply current to the RTD sensor to maintain the RTD sensor at a fixed temperature value (e.g., about 5 degrees Celsius, about 10 degrees Celsius) above the internal temperature, as measured by the chip thermistor. The current supplied to the RTD sensor can range from about 1 mA to about 30 mA. The total power applied to the RTD sensor can also be monitored and limited to about 0.1 mW to about 90 mW. By applying Equations 1 to 6 for pre-determined values of K, the ambient temperature can then be determined for the meter.

The time needed to determine the ambient temperature via the exemplary embodiments described herein can vary. In certain embodiments, the time to determine ambient temperature can range up to about 30 seconds. In certain embodiment, the time is less than about 20 seconds. In other embodiments, the time may exceed 30 seconds. In further embodiments, the ambient temperature can be determined in less than about 60 seconds. It can be particularly desirable to determine ambient temperature within the time ranges described herein for the described exemplary embodiments because such time ranges allow a user to obtain timely ambient temperature data appropriate for accurately determining, for example, temperature-sensitive fluid-analyte concentrations. The embodiments described herein are also useful for any temperature-sensitive application that requires accurate and up-to-date ambient temperature data. In the above non-limiting embodiment, the ambient temperature is determined to within about ±1 degree Celsius of the actual ambient temperature. Again, the above values apply to but one of numerous embodiments contemplated to fall within the present disclosure.

While the product of $k_{INSIDE}$ and $A_{INSIDE}$ can be approximated as being constant, the product may actually fluctuate over a wide temperature range. For example, in the above non-limiting embodiment, as the internal temperature fluctuates from 5 to 45 degrees Celsius, the product of $k_{INSIDE}$ and $A_{INSIDE}$ may range from about 0.56 at 5 degrees Celsius to about 0.63 at 45 degrees Celsius. Compensation for this fluctuation can be done for meters expected to be used over a wide operating temperature range by applying a linear fit or other best-fit equation to approximate the value for the product of $k_{INSIDE}$ and $A_{INSIDE}$.

As discussed above for Equations 3 and 4, once $\phi_{AMBIENT}$ is determined from known information about $\phi_{TOTAL}$ and $\phi_{INSIDE}$ at the steady state temperature, $T_{AMBIENT}$ can be determined from the product of $k_{AMBIENT}$ and $A_{AMBIENT}$, or $K_{AMBIENT}$, which is a derived constant that is specific to a given meter configuration. As discussed previously, $A_{INSIDE}$ is the internal surface area over which the heat flows, $A_{AMBIENT}$ is the external surface area over which the heat flows, and $k_{INSIDE}$ and $k_{AMBIENT}$ are fixed coefficients. The product of $k_{INSIDE}$ and $A_{INSIDE}$ ($K_{INSIDE}$) and the product of $k_{AMBIENT}$ and $A_{AMBIENT}$ ($K_{AMBIENT}$) are derived values for a specific meter configuration under certain operating conditions.

As discussed previously, a calibration process is performed to derive the values for $K_{INSIDE}$ and $K_{AMBIENT}$. In one non-limiting exemplary calibration process, the calibration is performed at a constant ambient temperature (e.g., about 25 degrees Celsius) with the RTD sensor operating at a fixed temperature value above the ambient temperature (e.g., about 25+10 degrees Celsius). As an initial step, any heat sources associated with the meter are turned off or removed, and the RTD sensor is maintained at 10 degrees Celsius above the internal temperature. Theoretically, the internal temperature of the meter will be higher than the ambient temperature due to, for example, the heat generated by the RTD sensor. However, the heat generated by the RTD sensor may be very small (e.g., between 10 to 20 mW), and thus, there may be no noticeable difference between the internal temperature of the meter and the ambient temperature when all other heat sources associated with the meter are isolated. In the next step, a heat source is activated within the meter, which raises the internal temperature of the meter. The temperature of the RTD sensor is maintained at a constant value above the internal temperature of the meter as determined by the chip thermistor (e.g., internal meter temperature+10 degrees Celsius). The power supplied to the RTD sensor is also monitored along with the internal temperature of the meter. The constants $K_{INSIDE}$ and $K_{AMBIENT}$ can then be calculated using Equations 7 and 8, which are based on maintaining the non-limiting and exemplary fixed constant of 10 degrees Celsius above the internal temperature:

$$K_{INSIDE} = (T_{INTERNAL\ HEAT} - T_{AMBIENT} - 10)/(P_{HEAT\ RTD} - P_{INITIAL\ RTD}) \quad \text{(Equation 7)}$$

$$K_{AMBIENT} = (P_{INITIAL\ RTD} - 10 * K_{INSIDE})/10 \quad \text{(Equation 8)}$$

where $T_{INTERNAL\ HEAT}$ is the internal temperature after applying the heat source;

$T_{AMBIENT}$ is the known ambient temperature;

$P_{HEAT\ RTD}$ is power supplied to RTD sensor through $T_{INTERNAL\ HEAT}$; and $P_{INITIAL\ RTD}$ is power supplied to RTD sensor before internal heating.

Other fixed constants are contemplated in addition to +10 degrees Celsius (e.g., +3 degrees, +5 degrees, +7 degrees, +15 degrees), which is only used for purposes of illustrating one demonstrative aspect of the present disclosure. Furthermore, other applied currents may be used to calibrate a meter depending on the desired operating conditions.

The temperature sensor embodiments disclosed herein provide an economical way to determine ambient temperature surrounding a meter that in turn provide multiple useful applications such as increased accuracy in determining sample temperature, minimizing human error while optimizing meter operations by allowing an auto-start capability in the meter once a desirable temperature range is reached, determining the readiness of the sample for testing based on the reagent falling within a desirable temperature range, and/or reducing temperature-related errors during analyte concentration determinations of a fluid sample.

Exemplary and non-limiting systems that may employ the above described temperature sensor embodiments are described further below in the example of FIGS. 3-5.

Figure 3:
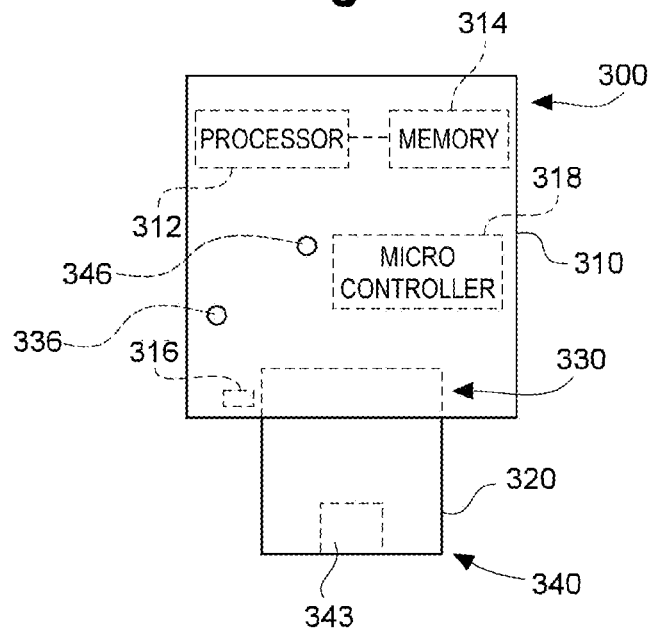
FIG. 3 illustrates a fluid analyte system including a meter and a test sensor according to one embodiment.

Turning now more generally to FIG. 3, a fluid analyte system 300 is illustrated including a meter 310 with a port for receiving and analyzing a fluid sample on a test sensor 320. The test sensor includes a connection end 330 where the test sensor 320 interfaces with the meter 310. The interface between the meter 310 and the test sensor 320 can allow the meter 310 to energize the test sensor 320 by applying, for example, a voltage difference across contacts on the test sensor and the meter. The test sensor 320 also includes a fluid-receiving end 340 for receiving a fluid sample into a fluid-receiving area 343 for subsequent analysis using the meter 310. A first temperature sensing element 316 can be positioned in close proximity to the fluid-receiving area 343 of the test sensor 320. In addition to, or alternatively, a second temperature sensing element 336 may be positioned within or at the surface of the shell or casing of the system 300.

Analytes that may be determined using the device include glucose, lipid profiles (for example, cholesterol, triglycerides, LDL and HDL), microalbumin, hemoglobin $A1_C$, fructose, lactate, or bilirubin. The present invention is not limited, however, to devices for determining these specific analytes, and it is contemplated that other analyte concentrations may be determined. The analytes may be in, for example, a whole blood sample, a blood serum sample, a blood plasma sample, or other body fluids like ISF (interstitial fluid) and urine.

In FIG. 3, the meter 310 receives and engages the test sensor 320. The meter 310 measures the concentration of analyte for the sample collected by the test sensor 320. The meter 310 can include contacts for the electrodes to detect the electrochemical reaction of an electrochemical test sensor. Alternatively, the meter 310 can include an optical detector to detect the degree of light alteration for an optical test sensor. To calculate the actual concentration of analyte from the electrochemical reaction measured by the meter 310 and to generally control the procedure for testing the sample, the meter 310 employs at least one processor 312, which may execute programmed instructions according to a measurement algorithm. Data processed by the processor 312 can be stored in a memory 314. The meter 310 may also use the same or a different processor for various operations, such as, for example, power management or temperature functions, including executing routines for temperature prediction of ambient temperature. Furthermore, the meter can include a user interface.

The temperature sensing elements 316, 336 can include, among other things, resistance temperature devices (see, e.g., FIGS. 1 and 2), thermistors, diode devices, etc. For non-RTD sensors, it is contemplated that temperature sensing elements 316, 336 will also include a nearby heat source (not shown) so that the heat flux through the system shell or casing can be determined. In addition, a third temperature sensing element 346 can be disposed within the interior of meter 310 to assess the internal meter temperature. The third temperature sensing element may be disposed on or near a PCB. In certain embodiments, the internal temperature sensor can also be embedded in a microcontroller 318 that is disposed within the meter 310. The third temperature sensor is connected to a processor or a microcontroller of the meter to allow absolute temperature readings to be collected within the meter itself. The meter 310 may also use the same or a different microcontroller or processor for power management, temperature prediction operations, data transfer operation, or to execute other routines associated with the meter 310.

Figure 4:
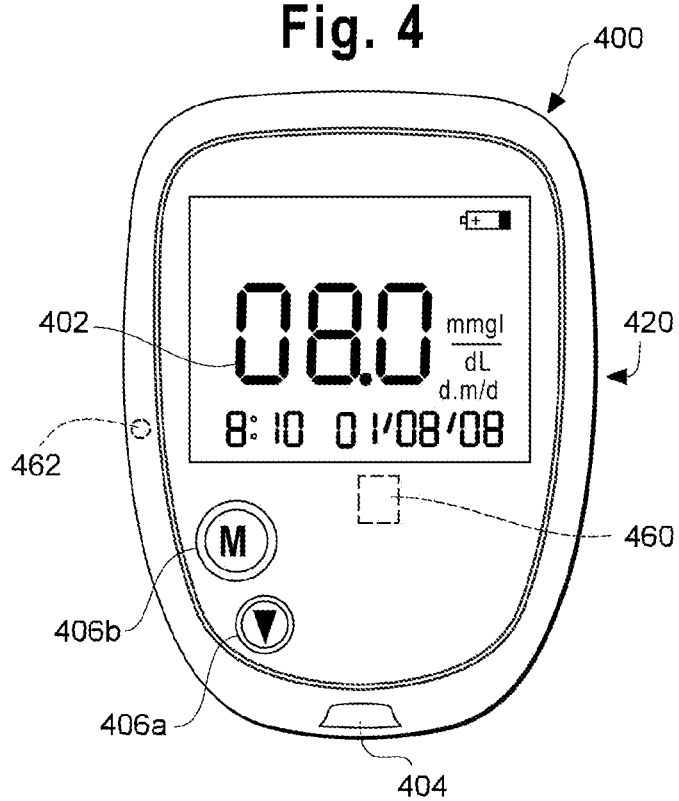
FIG. 4 illustrates a front view of a portable device according to another embodiment.

FIG. 4 illustrates an exemplary embodiment of a fluid analyte system. In particular, a portable meter 400 includes some or all of the elements discussed for the embodiments described in FIG. 3 and elsewhere herein. As shown in FIG. 4, the meter 400 includes a display 402 visible through a front portion 420, a test-sensor port 404, and a plurality of buttons 406a, 406b. After a user places a sample fluid on a test-sensor that is inserted into the test sensor port 404, the fluid analyte (e.g., glucose) level is determined by the meter 400, which displays the fluid analyte (e.g., glucose) reading on the display 402. The reading is then stored in the meter's memory device.

The meter 400 includes a microprocessor or the like for processing and/or storing data generated during the testing procedure. The meter 400 may also use the same or a different microprocessor for power management or temperature operations, including executing routines to control recharging operations of the meter 400 for battery-operated devices and for implementing temperature prediction algorithms in assessing ambient temperatures.

The test sensor port 404 is adapted to receive and/or hold a test sensor and assist in determining the analyte concentration of a fluid sample. A meter temperature may be monitored for the meter 400 with an internal meter temperature sensor 460 located within an inside area of the meter shell or casing. Another temperature sensor 462, such as an RTD sensor, may be embedded within or along a surface of the meter casing.

It is contemplated that in certain embodiments, the fluid analyte systems illustrated in FIGS. 3 and 4 can be configured to include a lancing device (not shown). For example, meters 300, 400 can be configured to receive and engage an element that collects a fluid sample. The meter 300, 400 can measure the concentration of analyte for the sample collected by the lancing device. The meter 300, 400 can also include contacts connected to electrodes that detect electrochemical reactions of an electrochemical test sensor within the lancing device. In certain embodiments, the fluid analyte system may be an integrated system that receives samples, processes analyte concentrations of fluid sample, and/or stores data within a self-contained system including the meter and lancing device.

FIGS. 5A and 5B illustrate an exemplary fluid analyte meter embodiment. Fluid analyte meter 500 can include some or all of the functionalities and components discussed for the embodiments described in FIGS. 3 and 4. For example, the fluid analyte meter 500 can be a portable blood glucose meter that is an integrated device with certain data processing and display features. A user can employ the fluid analyte meter 500 to analyze a blood sample by inserting a test sensor into port 520. A port light, such as, a port light emitting diode 525 may be disposed near the port 520 to illuminate the port area and assist the user with inserting the test sensor. The fluid analyte meter 500 can also include a battery 580 that may be recharged by a connection via a USB interface element 570 to either an external processing device (not shown), such as a PC, or other external power supply. If a rechargeable battery is used, a charging integrated circuit 545 may be included in meter 500 for recharging the battery 580. In certain embodiments, a battery may be disposed in a cap 502, which fits over the USB interface element 570. The meter 500 can also include a display 550 that provides information to a user of the meter 500. For example, the display 550 can include information on the battery strength, a calculated analyte concentration, historical analyte concentrations, date and time data, and power on/off information.

The fluid analyte meter 500 can also include one or more thermistors or other types of temperature sensing devices. For example, an RTD sensor 530 can be disposed within or at a surface of the outer casing or shell of the meter 500. A microcontroller with an embedded temperature sensor 540 can also be disposed within the meter 300 to determine the internal meter temperature. The RTD sensor 530 and/or temperature sensor 540 are connected to a processor or a microcontroller of the meter 500 to allow temperature readings to be collected. The meter 500 may also use the same or a different microcontroller or processor for power management, temperature prediction operations, data transfer operation, or to execute other routines associated with the meter 500. For example, temperature prediction algorithms can be implemented on the microcontroller or processor to determine an accurate ambient temperature for use in calculating an analyte concentration.

In certain embodiments, a fluid-analyte meter is configured to rapidly determine ambient temperature. The meter may include a housing defining an interior space and an exterior ambient space. The meter may also include a processor, a controller, a first and second temperature sensor, and a temperature-adjustment source. The processor may be disposed within the housing. The controller may also be disposed within the housing and be communicatively connected to the processor. The first temperature sensor may be disposed within the interior space of the housing. The second temperature sensor may be disposed on the housing and be communicatively connected to the controller. The temperature-adjustment source may be disposed on the housing and configured to create a convective zone about the second temperature sensor. The controller is configured to transmit instructions for supplying a variable current to the temperature-adjustment source such that the temperature-adjustment source adjusts the second temperature sensor to a predetermined steady-state temperature value different from a first temperature value. The first temperature value is based on first temperature data received via the controller from the first temperature sensor. The controller is further configured to receive second temperature data from the second temperature sensor. The controller or the processor is configured to determine an ambient temperature of the exterior ambient space based on the supplied current values, the predetermined steady-state temperature, and the first temperature values.

In certain embodiments, the fluid-analyte meter described above may also be configured with one or more of the following features. The fluid-analyte meter can be configured with the second temperature sensor and the temperature-adjustment source being a single element. The second temperature sensor can also be an RTD sensor. The temperature-adjustment source may also be a heat source and the pre-determined steady-state temperature value may be above the first temperature value. Alternatively, the temperature-adjustment source may be a thermoelectric cooler and the pre-determined steady-state temperature value may be below the first temperature value. The ambient temperature of the exterior space may be determined in less than one minute, or the ambient temperature of the exterior space may be determined in less than twenty seconds. It is also contemplated that the second temperature sensor is embedded in an interior surface of the housing. The second temperature sensor can also be embedded in an exterior surface of the housing. The second temperature sensor may also be at least partially embedded in a metal layer, where the metal layer is at least partially embedded in the housing. The meter can also include a printed circuit board disposed in the interior space of the housing with the first temperature sensor being disposed on the printed circuit board.

In certain embodiments, a method for rapidly determining ambient temperature in a fluid-analyte meter includes providing a meter including a housing with a first temperature sensor disposed within an interior space of the housing. A second temperature sensor is disposed on the housing, and a temperature-adjustment source is disposed near the second temperature sensor. A first temperature value is determined from first temperature data received via the first temperature sensor. A variable current is applied to the temperature-adjustment source such that the second temperature sensor is adjusted to a predetermined equilibrium temperature value different from the first temperature value. A second temperature value is determined from second temperature data received from the second temperature sensor. An ambient temperature of an exterior space of the fluid-analyte meter is determined based on the variable current and the determined first and second temperature values.

In certain embodiments, the method for rapidly determining ambient temperature can also include one or more of the following features. The second temperature sensor and the temperature-adjustment source can be a single element. The second temperature sensor can also be an RTD sensor. The temperature-adjustment source can be a heat source and the pre-determined equilibrium temperature value can be above the first temperature value. Alternatively, the temperature-adjustment source can be a thermoelectric cooler and the pre-determined equilibrium temperature value can be below the first temperature value. The second temperature sensor can be embedded in an interior surface or an exterior surface of the housing. The second temperature sensor can also be at least partially embedded in a metal layer, where the metal layer is at least partially embedded in the housing. The method can also include providing a printed circuit board disposed in the interior space of the housing, where the first temperature sensor is disposed on the printed circuit board.

In certain embodiments, a portable meter is configured to rapidly determine ambient temperature. The portable meter includes a housing, a processor, and a first and second temperature sensor. The housing defines an interior space and an area for receiving a fluid sample. The processor and the first temperature sensor are disposed within the interior space of the housing. The second temperature sensor is disposed on the housing. The processor is configured to determine a first temperature value from temperature data received from the first temperature sensor. The processor is further configured to apply a variable current to a temperature-adjustment source such that the second temperature sensor is adjusted to a predetermined steady-state temperature value different from the first temperature value. The processor is also configured to determine an ambient temperature of an exterior space of the housing based on the applied variable current, the pre-determined steady-state temperature value, and the received first temperature value.

In certain embodiments, the above portable meter is configured to include one or more of the following features. The second temperature sensor and the temperature-adjustment source can be a single element comprising an RTD sensor. The second temperature sensor can be embedded in an interior surface of the housing. The second temperature sensor can be embedded in an exterior surface of the housing. The second temperature sensor can be at least partially embedded in a heat conductive layer, with the heat conductive layer is at least partially embedded in the housing. The portable meter can also include a printed circuit board disposed in the interior space of the housing, with the first temperature sensor and the processor being disposed on the printed circuit board. The temperature-adjustment source can be a heat source and the pre-determined steady-state temperature value can be above the first temperature value. Alternatively, the temperature-adjustment source is a thermoelectric cooler and the pre-determined steady-state temperature value can be below the first temperature value. A heat flux from the second temperature sensor to the interior space of the housing may be approximately constant upon attaining the predetermined steady-state temperature value at the second temperature sensor. A total applied energy can also be determined based on the applied variable current. It is also contemplated that the ambient temperature of the exterior space can be determined in less than one minute, or in less than twenty minutes.

It would be understood within the field of the present disclosures that elements and/or components of the meter modules and/or portable devices described herein can be embodied in a single device or in multiple devices in various configurations of elements and/or components. Furthermore, it would be understood that the devices described herein can be used in portable or non-portable fluid analyte meters.

Thus, while the meter modules or portable devices described herein may be portable, the present disclosures can also be applied to non-portable fluid analyte meters.

While the invention has been described with reference to details of the illustrated embodiments, these details are not intended to limit the scope of the invention as defined in the appended claims. For example, although the illustrated embodiments are generally described for RTD sensors on the casing or shell of a meter, other temperature sensors may be used that are associated with a heat source. Furthermore, different types of temperature sensors may be used to determine the temperature of the inside area of the meter. In addition, the calibration process may be modified for a specific meter application generally using the procedures described herein. In addition, it should be noted that the cross-section of the meters and test sensors used herein may be other shapes such as circular, square, hexagonal, octagonal, other polygonal shapes, or oval. The non-electrical components of the illustrated embodiments are often made of a polymeric material. Non-limiting examples of polymeric materials that may be used in forming the meter include polycarbonate, ABS, nylon, polypropylene, or combinations thereof. It is contemplated that the fluid analyte systems can also be made using non-polymeric materials. The disclosed embodiments and obvious variations thereof are contemplated as falling within the spirit and scope of the claimed invention.

What is claimed are:

1. A portable meter configured to rapidly determine ambient temperature, the portable meter comprising:
   a housing defining an interior space and an area for receiving a fluid sample;
   a first processing unit and a first temperature sensor disposed within said interior space of said housing; and
   a second temperature sensor disposed on said housing,
   wherein said first processing unit or another processing unit is configured to:
      determine a first temperature value from temperature data received from said first temperature sensor;
      apply a variable current to a temperature-adjustment source such that said second temperature sensor is adjusted to a predetermined steady-state temperature value different from said first temperature value; and
      determine an ambient temperature of an exterior space of said housing based on said applied variable current, said pre-determined steady-state temperature value, and said received first temperature value, said ambient temperature value being determined in less than about sixty seconds.

2. The portable meter of claim 1, wherein said second temperature sensor and said temperature-adjustment source are a single element comprising an RTD sensor.

3. The portable meter of claim 1, wherein said second temperature sensor is embedded in an interior surface of said housing.

4. The portable meter of claim 1, wherein said second temperature sensor is embedded in an exterior surface of said housing.

5. The portable meter of claim 1, wherein said second temperature sensor is at least partially embedded in a heat conductive layer, said heat conductive layer being at least partially embedded in said housing.

6. The portable meter of claim 1, further comprising providing a printed circuit board disposed in said interior space of said housing, said first temperature sensor and said first processing unit being disposed on said printed circuit board.

7. The portable meter of claim 1, wherein said temperature-adjustment source is a heat source and said pre-determined steady-state temperature value is greater than said first temperature value.

8. The portable meter of claim 1, wherein said temperature-adjustment source is a thermoelectric cooler and said pre-determined steady-state temperature value is less than said first temperature value.

9. The portable meter of claim 1, wherein upon attaining said predetermined steady-state temperature value at said second temperature sensor, a heat flux from said second temperature sensor to said interior space of said housing is approximately constant.

10. The portable meter of claim 1, wherein said first processing unit or another processing unit is further configured to determine a total applied energy based on said applied variable current.

11. The portable meter of claim 1, wherein said ambient temperature of said exterior space is determined in less than twenty seconds.

12. A method for rapidly determining ambient temperature in a fluid-analyte meter, the method comprising:
providing a meter including a housing, a first temperature sensor disposed within an interior space of said housing, a second temperature sensor disposed on said housing, and a temperature-adjustment source disposed near said second temperature sensor such that said temperature-adjustment source is configured to create a convective zone about said second temperature sensor;
determining a first temperature value from first temperature data received via said first temperature sensor;
applying a variable current to said temperature-adjustment source such that said second temperature sensor is adjusted to a predetermined equilibrium temperature value different from said first temperature value; and
determining an ambient temperature of an exterior space of said housing, said ambient temperature based on said applied variable current, said predetermined equilibrium temperature value, and said received first temperature value, said ambient temperature value being determined in less than about sixty seconds.

13. The method of claim 12, wherein said ambient temperature value of said exterior space is determined in less than about twenty seconds.

14. The method of claim 12, further comprising providing a printed circuit board disposed in said interior space of said housing, said first temperature sensor being disposed on said printed circuit board.

15. The method of claim 12, wherein said second temperature sensor is embedded in an interior surface of said housing.

16. The method of claim 12, wherein said second temperature sensor is embedded in an exterior surface of said housing.

17. The method of claim 12, wherein said temperature-adjustment source is a heat source and said pre-determined equilibrium temperature value is greater than said first temperature value.

18. The method of claim 12, wherein said temperature-adjustment source is a thermoelectric cooler and said equilibrium temperature value is less than said first temperature value.

19. The method of claim 12, wherein upon attaining said predetermined equilibrium temperature value at said second temperature sensor, a heat flux from said second temperature sensor to an interior space defined by said housing is approximately constant.

20. The method of claim 12, wherein said first processing unit or another processing unit is further configured to determine a total applied energy based on said applied variable current.

* * * * *